US012048542B2

(12) United States Patent
Wilkinson et al.

(10) Patent No.: US 12,048,542 B2
(45) Date of Patent: Jul. 30, 2024

(54) SQUEEZE ACTIVATED BLOOD COLLECTION SET

(71) Applicant: Becton, Dickinson and Company, Franklin Lakes, NJ (US)

(72) Inventors: Bradley M. Wilkinson, North Haledon, NJ (US); C. Mark Newby, Kamas, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 542 days.

(21) Appl. No.: 17/051,339

(22) PCT Filed: Apr. 30, 2019

(86) PCT No.: PCT/US2019/029938
§ 371 (c)(1),
(2) Date: Oct. 28, 2020

(87) PCT Pub. No.: WO2019/213097
PCT Pub. Date: Nov. 7, 2019

(65) Prior Publication Data
US 2021/0369159 A1      Dec. 2, 2021

Related U.S. Application Data

(60) Provisional application No. 62/665,108, filed on May 1, 2018.

(51) Int. Cl.
*A61B 5/15*       (2006.01)
(52) U.S. Cl.
CPC .... *A61B 5/150641* (2013.01); *A61B 5/15003* (2013.01); *A61B 5/150389* (2013.01);
(Continued)

(58) Field of Classification Search
CPC ........ A61B 5/150641; A61B 5/150389; A61B 5/150519; A61B 5/150732;
(Continued)

(56) References Cited

U.S. PATENT DOCUMENTS 4,735,618 A     4/1988   Hagen
4,776,849 A    10/1988   Shinno et al.
(Continued)

FOREIGN PATENT DOCUMENTS

CN         1556717 A    12/2004
CN       101069633 A    11/2007
(Continued)

*Primary Examiner* — Yi-Shan Yang
*Assistant Examiner* — Om Patel
(74) *Attorney, Agent, or Firm* — The Webb Law Firm

(57) ABSTRACT

A shieldable needle device (12) with a needle cannula (28), a hub (44) supporting the needle cannula, and a tip guard (24) axially movable along the needle cannula where, upon transition, the tip guard protectively surrounds the distal end (42) of the needle cannula. The needle device includes a pair of wings (60) extending laterally from opposing sides of the tip guard and connected to the hub. The pair of wings are transitionable between a first position and a second position, wherein transition of the pair of wings advances the tip guard from a proximal position to a shielding distal position. The wings include protrusions (66) which cause the longitudinal axis of the needle cannula to become offset from the opening (52) of the tip guard during advancement of the tip guard preventing the needle cannula from being reinserted through the tip guard after the tip guard has been transitioned to the distal position.

22 Claims, 11 Drawing Sheets

(52) U.S. Cl.
CPC .. *A61B 5/150519* (2013.01); *A61B 5/150732* (2013.01); *A61B 5/15074* (2013.01); *A61B 5/150259* (2013.01)

(58) Field of Classification Search
CPC .......... A61B 5/15074; A61B 5/150259; A61B 5/154; A61B 5/153; A61B 5/150503; A61B 5/150717; A61B 5/15–15003; A61B 5/150267–15029; A61B 5/150633–150755; A61B 5/150885–150923; A61M 5/3275; A61M 5/3202; A61M 2005/3247; A61M 25/0625; A61M 25/0637
See application file for complete search history.

(56) References Cited

U.S. PATENT DOCUMENTS

| | | | |
|---|---|---|---|
| 5,120,320 A | 6/1992 | Fayngold |
| 5,192,275 A | 3/1993 | Burns |
| 5,295,974 A | 3/1994 | O'Laughlin |
| 5,324,302 A | 6/1994 | Crouse |
| 5,531,704 A | 7/1996 | Knotek |
| 5,951,525 A | 9/1999 | Thone et al. |
| 6,482,180 B2 | 11/2002 | Toyokawa et al. |
| 6,673,047 B2 | 1/2004 | Crawford et al. |
| 6,743,186 B2 | 6/2004 | Crawford et al. |
| 6,786,891 B2 | 9/2004 | Hiejima |
| 6,832,992 B2 | 12/2004 | Wilkinson |
| 6,835,190 B2 | 12/2004 | Nguyen |
| 6,855,130 B2 | 2/2005 | Saulenas et al. |
| 6,932,803 B2 | 8/2005 | Newby |
| 7,112,190 B2 | 9/2006 | Bressler et al. |
| 7,150,725 B2 | 12/2006 | Wilkinson |
| 7,175,610 B2 | 2/2007 | Mori |
| 7,201,740 B2 | 4/2007 | Crawford |
| 7,326,189 B2 | 2/2008 | Mori |
| 7,578,805 B2 | 8/2009 | Hwang |
| 7,803,138 B2 | 9/2010 | Bressler et al. |
| 7,955,310 B2 | 6/2011 | Hirota et al. |
| 8,052,641 B2 | 11/2011 | Hiejima et al. |
| 8,133,207 B2 | 3/2012 | Wilkinson |
| 8,182,451 B2 | 5/2012 | Bressler et al. |
| 8,187,230 B2 | 5/2012 | Tanabe et al. |
| 8,425,472 B2 | 4/2013 | Bressler et al. |
| 8,496,626 B2 | 7/2013 | Hiraoka et al. |
| 8,617,122 B2 | 12/2013 | Judd et al. |
| 8,708,977 B2 | 4/2014 | Bressler et al. |
| 9,387,150 B2 | 7/2016 | Okihara |
| 9,585,610 B2 | 3/2017 | Terasawa et al. |
| 10,258,772 B2 | 4/2019 | Bauer et al. |
| 10,524,710 B2 | 1/2020 | Wilkinson |
| 10,646,149 B2 | 5/2020 | Crawford et al. |
| 10,987,473 B2 | 4/2021 | Horvath et al. |
| 2001/0053892 A1* | 12/2001 | Parmigiani ......... A61M 5/3275 128/919 |
| 2002/0099339 A1 | 7/2002 | Niermann |
| 2003/0181871 A1* | 9/2003 | Wilkinson ........ A61M 25/0637 604/263 |
| 2003/0220587 A1 | 11/2003 | Swenson |
| 2004/0143226 A1* | 7/2004 | Marsden .......... A61B 5/150671 604/272 |
| 2004/0240371 A1 | 12/2004 | Suzuki |
| 2006/0229532 A1* | 10/2006 | Wong ............... A61B 5/150358 600/583 |
| 2008/0306452 A1 | 12/2008 | Crawford |
| 2009/0163875 A1* | 6/2009 | Hiraoka ............. A61M 5/158 604/192 |
| 2011/0301551 A1 | 12/2011 | Koehler et al. |
| 2018/0221592 A1* | 8/2018 | Brugger .................. A61M 5/50 |

FOREIGN PATENT DOCUMENTS

| | | |
|---|---|---|
| CN | 101104089 A | 1/2008 |
| CN | 103637809 A | 3/2014 |
| EP | 1348462 A1 | 10/2003 |
| JP | 8164122 A | 6/1996 |
| JP | 966106 A | 3/1997 |
| JP | 200393515 A | 4/2003 |
| JP | 200433734 A | 2/2004 |
| JP | 201544114 A | 3/2015 |
| WO | 9951290 A1 | 10/1999 |
| WO | 03026731 A1 | 4/2003 |
| WO | 2007141603 A2 | 12/2007 |

\* cited by examiner

SQUEEZE ACTIVATED BLOOD COLLECTION SET

CROSS-REFERENCE TO RELATED APPLICATIONS

This application is the United States national phase of International Application No. PCT/US2019/029938 filed Apr. 30, 2019, and claims priority to U.S. Provisional Application Ser. No. 62/665,108, entitled "Squeeze Activated Blood Collection Set", and filed May 1, 2018, the entire disclosures of which are hereby incorporated by reference in their entirety.

BACKGROUND OF THE INVENTION

Field of the Invention

The present disclosure relates to blood collection sets for safe and convenient handling of needles. More particularly, the present disclosure relates to a shieldable needle device for a blood collection set having user controlled shield activation.

Description of Related Art

A blood collection set or intravenous (IV) infusion set typically includes a needle cannula having a proximal end, a pointed distal end and a lumen extending therebetween. The proximal end of the needle cannula is securely mounted in a plastic hub with a central passage that communicates with the lumen through the needle cannula. A thin flexible thermoplastic tube is connected to the hub and communicates with the lumen of the needle cannula. The end of the plastic tube remote from the needle cannula may include a fixture for connecting the needle cannula to a blood collection tube or some other receptacle. The specific construction of the fixture will depend upon the characteristics of the receptacle to which the fixture will be connected.

In order to reduce the risk of incurring an accidental needle-stick wound, protection of used needle tips becomes important. With concern about infection and transmission of diseases, methods and devices to enclose the used disposable needle have become very important and in great demand. For example, needle assemblies commonly employ a safety shield that can be moved into shielding engagement with a used needle cannula without risking an accidental needle-stick.

Some needle shields are referred to as tip guards, and include a small rigid guard that can be telescoped along the length of a needle cannula and extended over the puncture tip of the needle for protection. Such conventional tip guards may include some form of tether for limiting the travel of the tip guard to the length of the needle cannula. Additionally, such conventional tip guards typically include a structure that lockingly engages over the tip of the used needle cannula to prevent both accidental and intentional re-exposure of the needle. The structure for preventing re-exposure may include a metallic spring clip or a transverse wall integrally formed with one end of the tip guard. Needle assemblies including such tip guards, however, typically include extensive mechanics for positioning of the tip guard, resulting in complex arrangements, which are costly to manufacture and assemble. Also, operation of the tip guard can involve substantial manipulation by the user to extend the tip guard to a shielding position.

While prior art devices provide for effective shielding of used needles, a need remains for needle assemblies for use with a blood collection set, which achieve secure and effective shielding of a used needle tip, which is simple and inexpensive to manufacture and easy to operate.

SUMMARY OF THE INVENTION

The present disclosure is directed to a shieldable needle device, particularly useful in connection with a blood collection set. The needle device includes a needle cannula having proximal and distal ends and a hub supporting at least a portion of the needle cannula. A tip guard is axially movable along the needle cannula from a proximal position adjacent the hub such that at least the distal end of the needle extends through an opening defined in the tip guard to a distal position where the tip guard protectively surrounds the distal end of the needle cannula. A pair of wings extend laterally from opposing sides of the tip guard and are connected to the hub. The pair of wings are transitionable between a first position and a second position, wherein transition of the pair of wings from the first position to the second position advances the tip guard from the proximal position to the distal position. A longitudinal axis of the needle cannula is offset from the opening of the tip guard to prevent the needle cannula from being reinserted through the tip guard after the tip guard has been transitioned to the distal position.

The tip guard biases the needle cannula, such that, at least the distal end of the needle cannula extends through the tip guard when the tip guard is in the proximal position. At least one of the pair of wings or both of the wings can comprise a protrusion for contacting the needle cannula when the tip guard is in the distal position to bias the needle cannula in the offset position to prevent the needle cannula from being reinserted through the tip guard. A first protrusion can be provided on a first one of the pair of wings at a first distance from the tip guard and a second protrusion can be provided on the other one of the pair of wings at a second distance from the tip guard. The first distance can be different from the second distance. The wings can extend laterally in the first position and proximally in the second position. Each of the wings can be connected to the hub by a bendable arm, each bendable arm extending laterally from opposing sides of the hub, wherein a locking edge is provided on at least one of the bendable arms. According to one embodiment, the bendable arms extend laterally from the hub when the tip guard is in the proximal position and collapse toward the longitudinal axis of the tip guard when the tip guard is in the distal position.

The hub can further comprise a locking member adapted to engage with the locking edge to lock the pair of wings in the second position. According to one embodiment, the locking member can comprise a one-way barb. The needle device is designed so that when the locking member engages with the locking edge, the locking member is locked to the at least one of the bendable arms at a location proximal to the pair of wings.

The tip guard can be releasably connected to the hub when the tip guard is in the proximal position and the hub can be friction fit within a recess defined in the tip guard when the tip guard is in the proximal position. According to one design, the hub and the tip guard can be connected via a frangible tab when the tip guard is in the proximal position and this frangible tab can be broken when an inwardly directed force is applied to the pair of wings.

The needle device can also include a dorsal fin extending from the hub and a removable cover protectively surrounding the needle cannula when the tip guard is in the proximal position. Gripping tips can be provided on each of the pair of wings. The device can also include a flexible tube extending from the proximal end of the hub, the flexible tube including structure for mating with a blood collection assembly.

The present disclosure is also directed to a blood collection set comprising a shieldable needle device including a needle cannula having proximal and distal ends and a hub supporting at least a portion of the needle cannula. The needle device further includes a tip guard axially movable along the needle cannula from a proximal position adjacent the hub, such that, at least the distal end of the needle extends through an opening defined in the tip guard to a distal position where the tip guard protectively surrounds the distal end of the needle cannula. The collection set includes a pair of wings extending laterally from opposing sides of the tip guard and connected to the hub, the pair of wings transitionable between a first position and a second position, wherein transition of the pair of wings from the first position to the second position advances the tip guard from the proximal position to the distal position. A protrusion is positioned on at least one of the pair of wings for engaging the needle cannula, when the tip guard is in the distal position to bias the needle cannula offset from the opening of the tip guard to prevent the needle cannula from being reinserted into the tip guard after the tip guard has been transitioned to the distal position. The collection set further includes a flexible tube having a first end and a second end, the first end of the flexible tube connected to the proximal end of the hub and a blood collection assembly secured to the second end of the flexible tube. According to one embodiment, the blood collection assembly can comprise a tube holder and an integrated non-patient cannula. The tube holder can be adapted to receive an evacuated specimen collection container therein.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DESCRIPTION OF THE INVENTION

Figure 1:
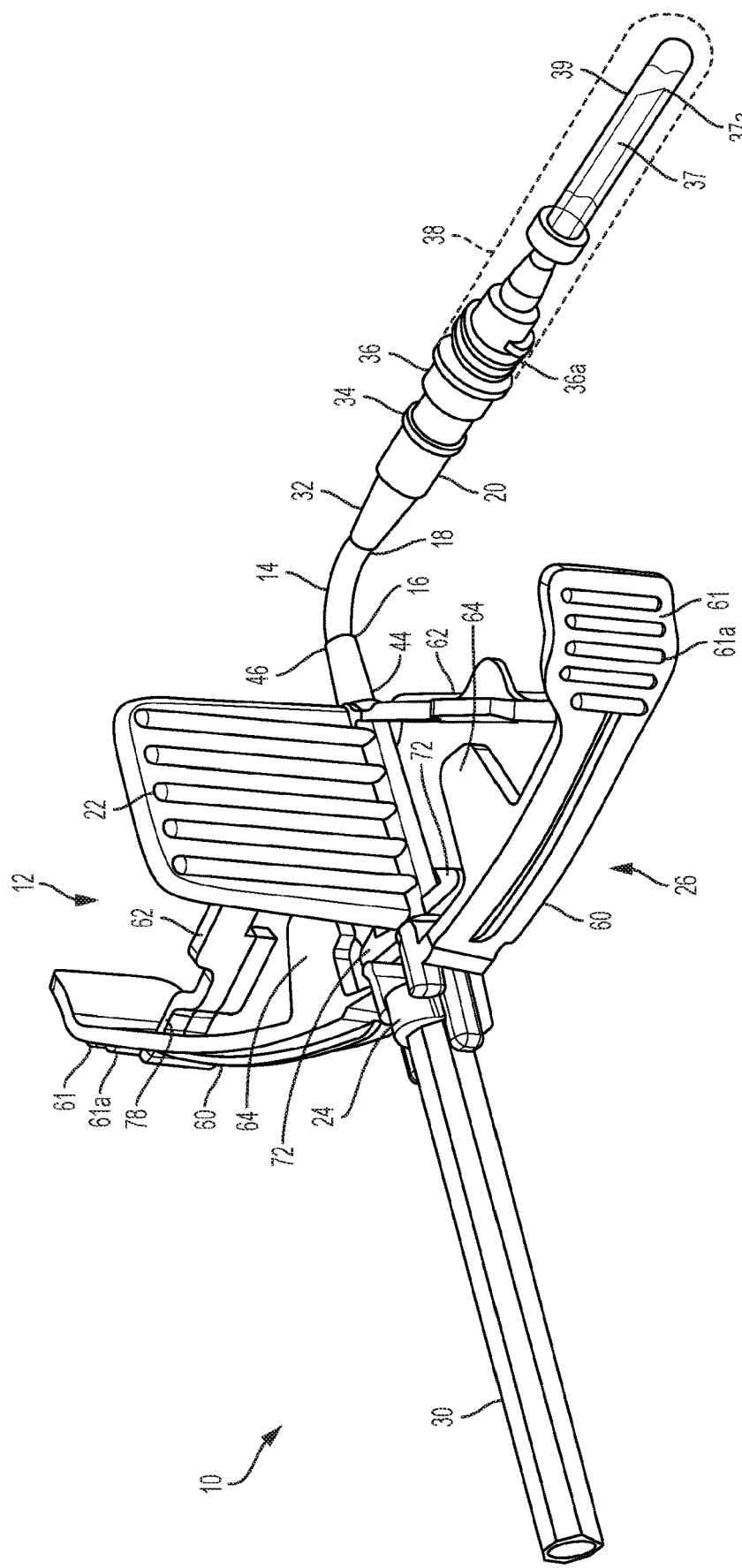
FIG. 1 is a perspective view of the blood collection set, including the shieldable needle device, in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Figure 2:
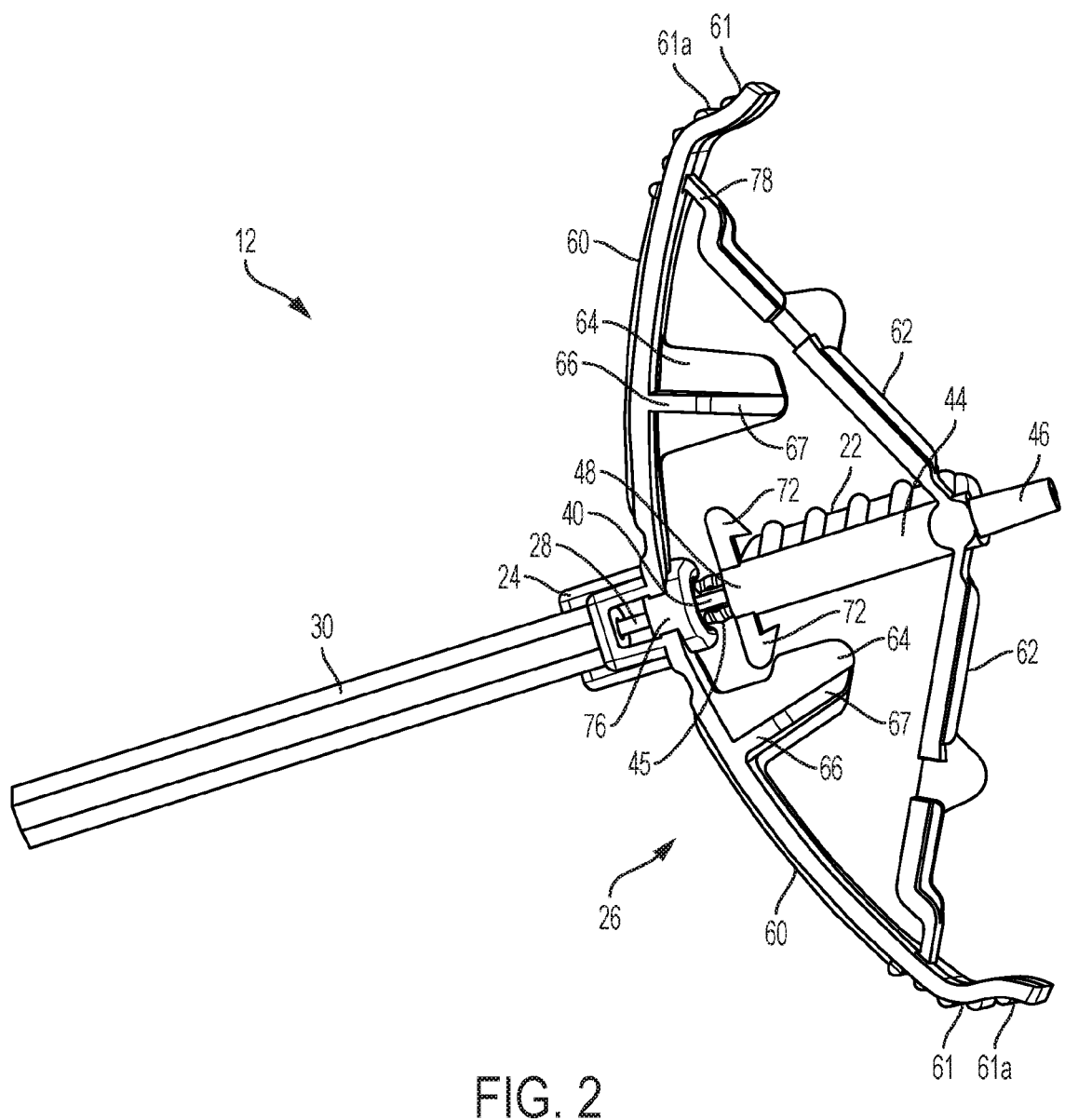
FIG. 2 is a bottom perspective view of the shieldable needle device of FIG. 1, in accordance with an embodiment of the present invention.

Reference is now made to FIGS. 1 and 2 which show the blood collection set generally indicated as 10, including the shieldable needle device generally indicated as 12, in accordance with an embodiment of the present invention. The blood collection set 10 may include the needle device 12, a length of flexible plastic tubing 14 associated with a proximal fitting 20, a grip 22, a tip guard 24, tip guard advancing system generally indicated as 26, and a needle cannula 28 fitted with a cannula guard 30.

The tubing 14 includes a first or distal end 14 associated with the needle device 12, a second or proximal end 18 associated with the proximal fitting 20, and a passage extending between the ends. Tubing 14 may be a conventional intravenous tubing used in conventional blood collection sets or infusion sets. According to one embodiment, the proximal fitting 20 can be molded unitarily from a plastic material and includes a proximal end 32, a distal end 34, and a passage extending between the ends. Portions of the passage adjacent distal end 34 are configured to telescope tightly over proximal end 18 of tubing 14 so that the passage through tubing 14 communicates with the passage through proximal fitting 20. Adhesive, welding, or the like can be employed to achieve a permanent connection between tubing 14 and proximal fitting 20. According to one design, the proximal end 32 of fitting 20 defines a female luer connector that can be mated with an appropriate male luer connector. The male luer connector may include a proximal needle cannula that can be placed in communication with an evacuated tube. Alternatively, a male luer connector at the distal end of a conventional prior art syringe can be connected directly to proximal fitting 20 for infusing a medication into the patient. In this instance, a separate male luer cap can be provided for closing the proximal end of connector 20. Other fittings may be engaged threadedly with proximal fitting 20 to achieve specific intended applications. Additionally, proximal fittings 20 of other configurations may be employed to achieve a particular objective. According to one embodiment, the proximal fitting can include a connector and/or a hub 36 associated therewith, wherein the hub has a non-patient cannula 37 secured thereto. The hub 36 can include threads 36a thereon for attachment with a tube holder 38, which is adapted to receive an evacuated specimen collection container (not shown) therein. The non-patient cannula 37 can include a tip 37a and a flexible sleeve 39 can be provided to cover the non-patient cannula 37 and cannula tip 37a.

Figure 3:
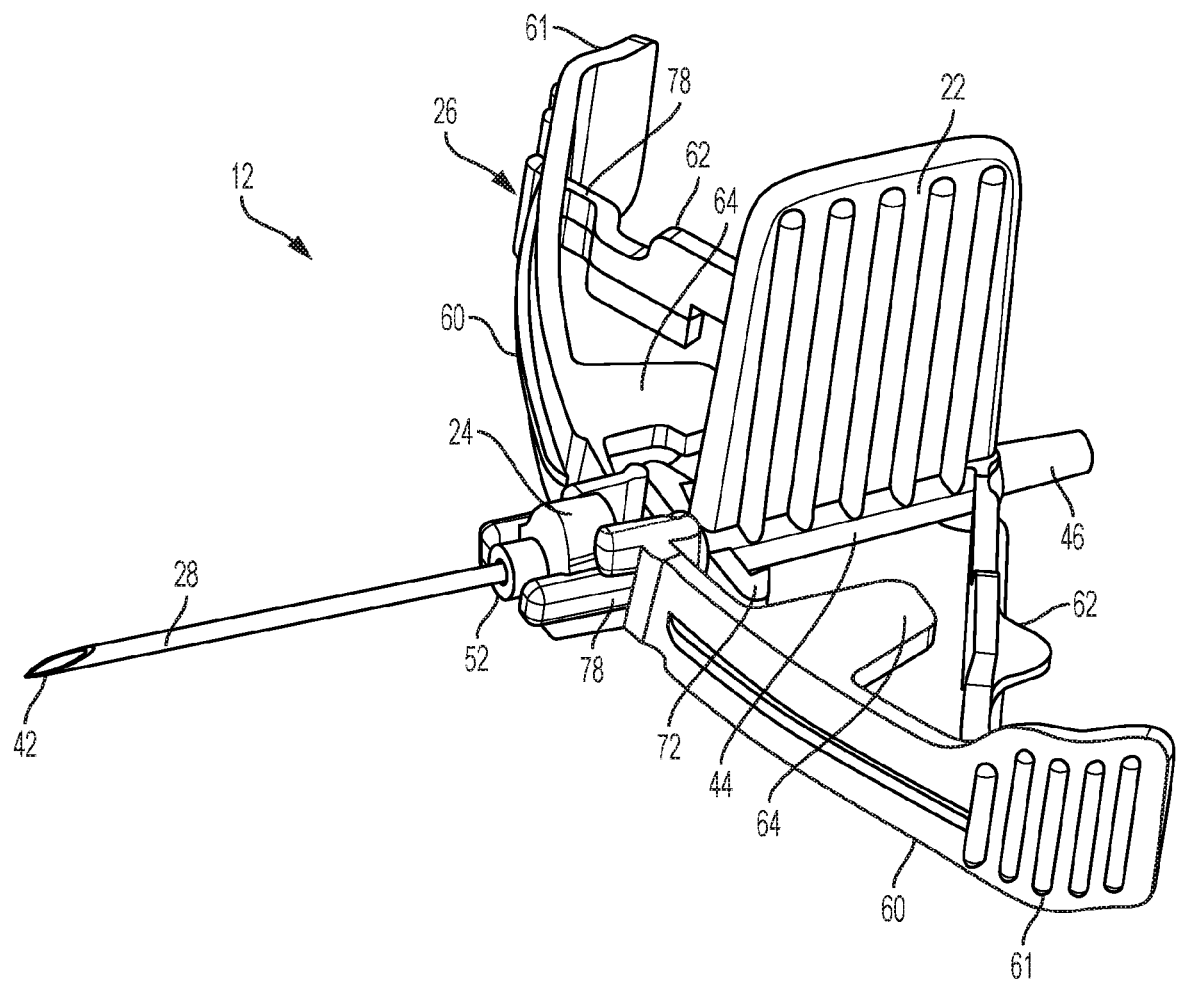
FIG. 3 is a perspective view of the shieldable needle device of FIG. 1, with the cannula shield removed and with the tip guard in a retracted proximal position, in accordance with an embodiment of the present invention.
Figure 4:
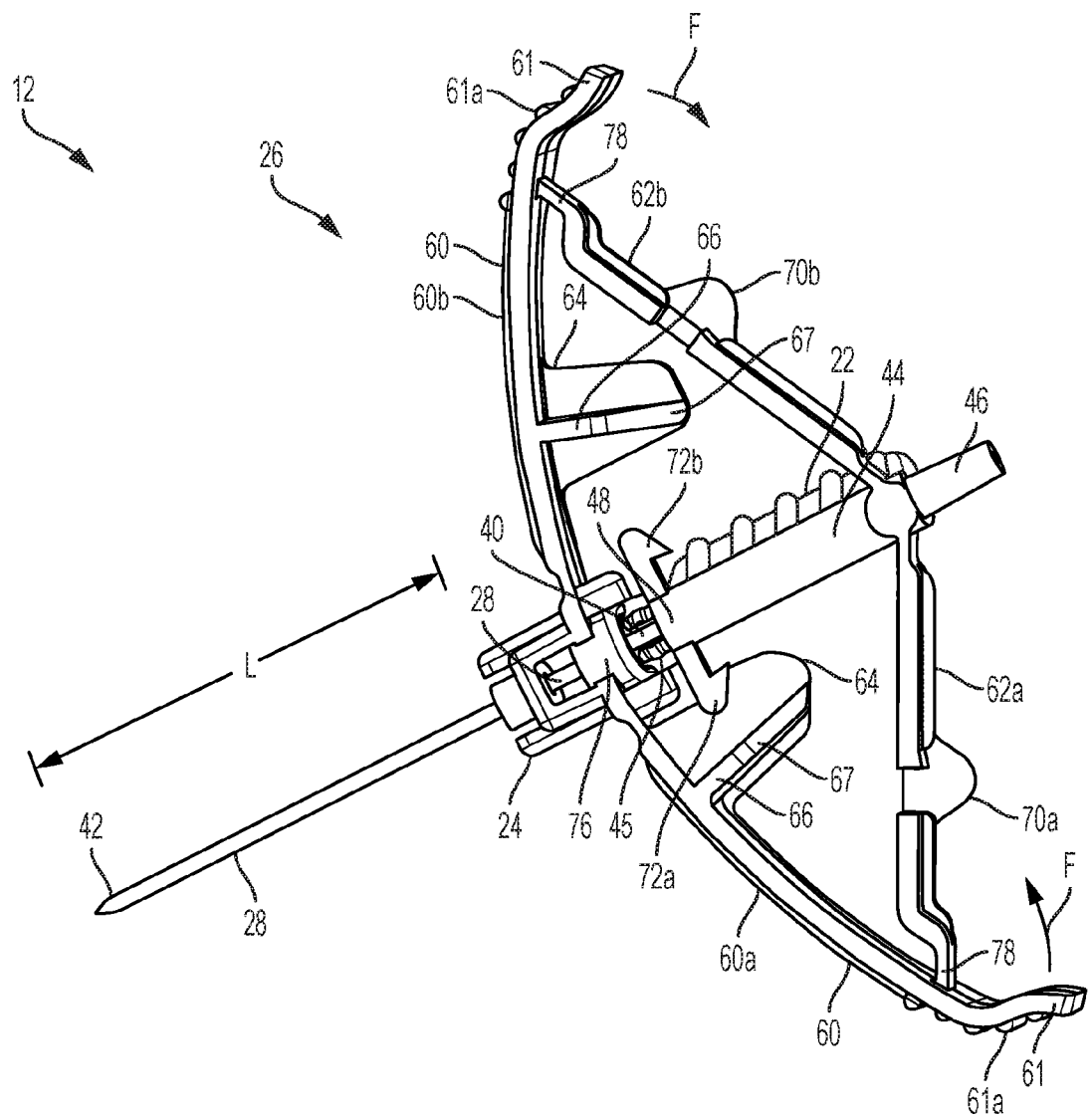
FIG. 4 is a bottom perspective view of the shieldable needle device of FIG. 3, in accordance with an embodiment of the present invention.

With continuing reference to FIGS. 1 and 2, and with further reference to FIGS. 3-4, the needle cannula 28 has a proximal end 40 and a distal end 42 and a lumen extending between the ends. Distal end 42 of needle cannula 28 is beveled to a sharp tip. A hub 44 is provided for supporting at least a portion of the needle cannula 28. Needle hub 44 can be molded unitarily from a plastic material, such as, polycarbonate, polypropylene, polyethylene, acrylic, polystyrene and acrylonitrile butadiene styrene (ABS). According to one design, the needle hub 44 can be molded from a transparent or translucent material to enable observation of blood or other fluid flowing through needle hub 44.

Needle hub 44 includes a proximal end 46, a distal end 48 and a passage (not shown) extending between the ends. Portions of the passage adjacent proximal end 46 are dimensioned to receive distal end 16 of tubing 14. According to one embodiment, the distal end 16 of tubing 14 can be telescoped into the passage of needle hub 44 and bonded in position adjacent proximal end 46, of needle hub 44. Portions of the passage adjacent distal end 48 of needle hub 44 are dimensioned for slidable receipt of proximal end 40 of needle cannula 28. According to one design, the proximal end 40 of needle cannula 34 can be secured permanently to needle hub 44 by epoxy or another well-known adhesive and/or by a mechanical affixation. Cannula guard 30 is a rigid cylindrical tube with a length that exceeds the projecting length of needle cannula 28 from needle hub 44. Cannula guard 30 is sized such that it can be telescoped over needle cannula 28 and frictionally retained on the tip guard distal 24.

Figure 5:
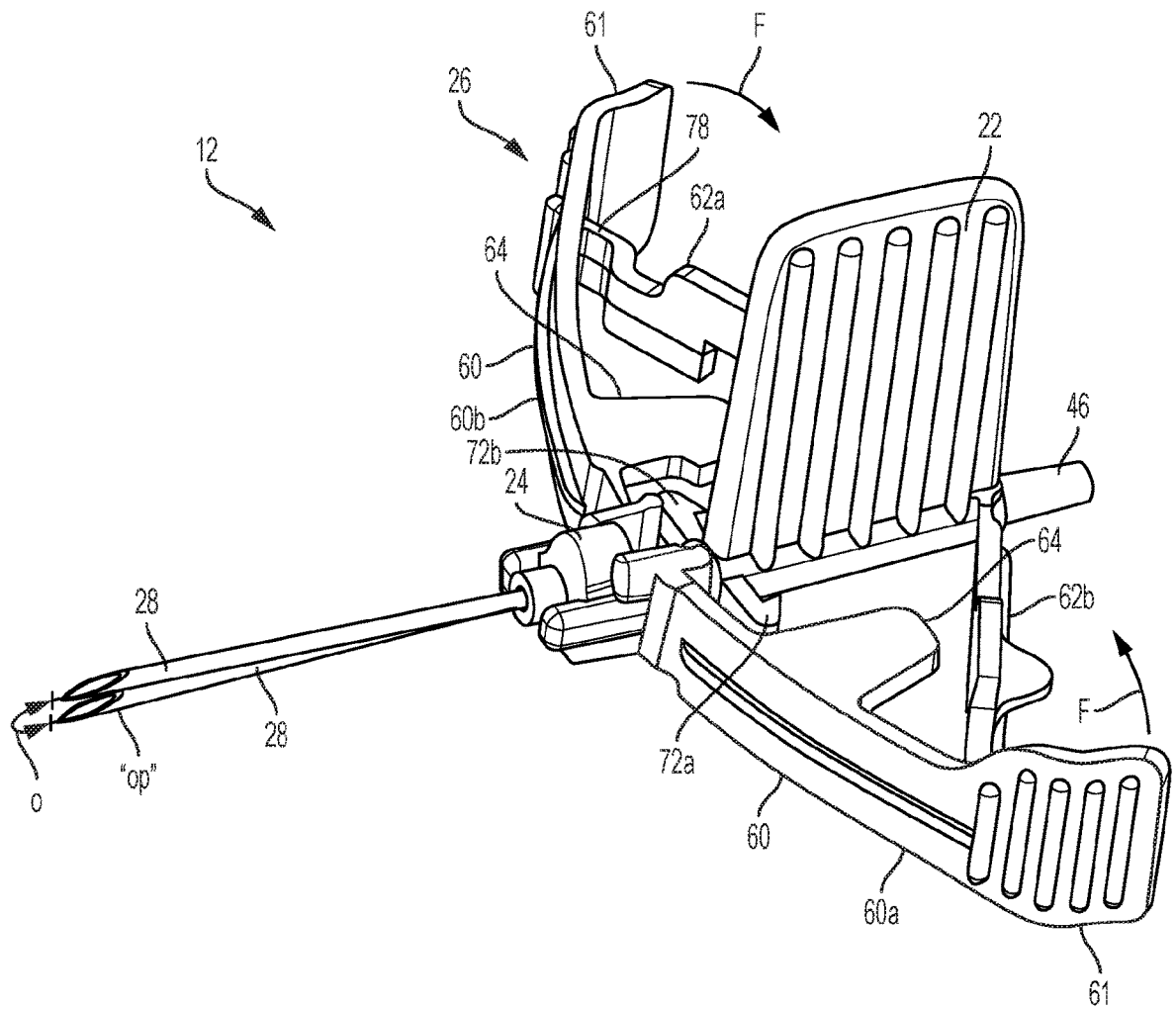
FIG. 5 is a perspective view of the shieldable needle device of FIG. 3, showing, for illustrative purposes, the deflection of the needle cannula to an offset position that occurs due to contact of the needle cannulas with the wing protrusions during transition of the tip guard from a retracted proximal position to an extended distal position, in accordance with an embodiment of the present invention.
Figure 5A:
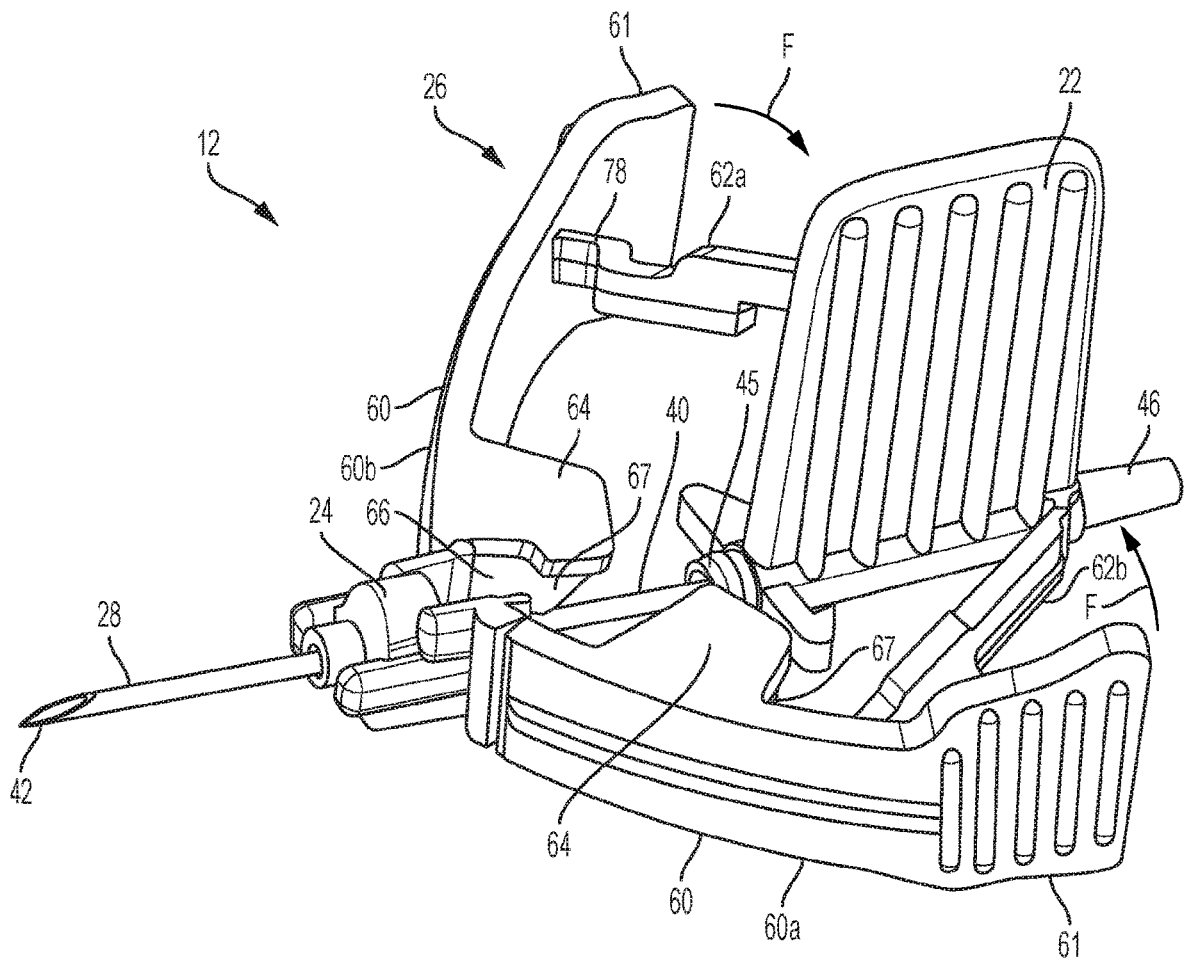
FIG. 5A is a perspective view of the shieldable needle device of FIG. 3 during transition of the tip guard from the retracted proximal position to the extended distal position in accordance with an embodiment of the present invention.
Figure 5B:
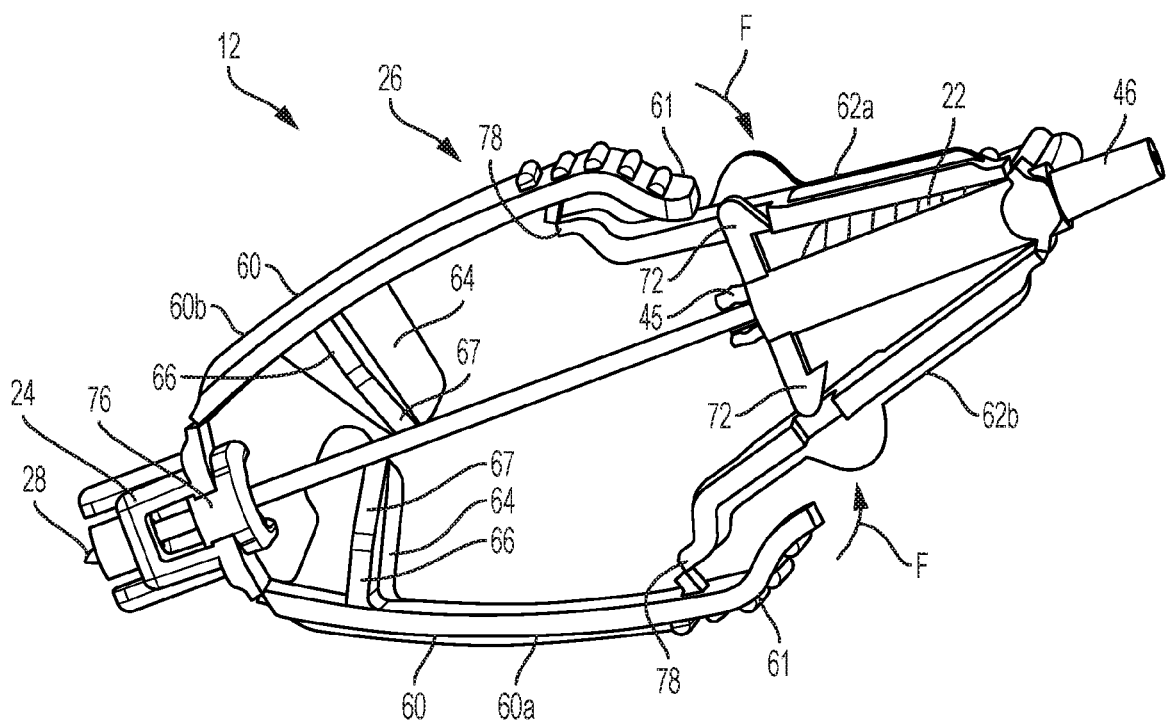
FIG. 5B is a bottom perspective view of the shieldable needle device of FIG. 3 during transition of the tip guard from the retracted proximal position to the extended distal position in accordance with an embodiment of the present invention.
Figure 6:
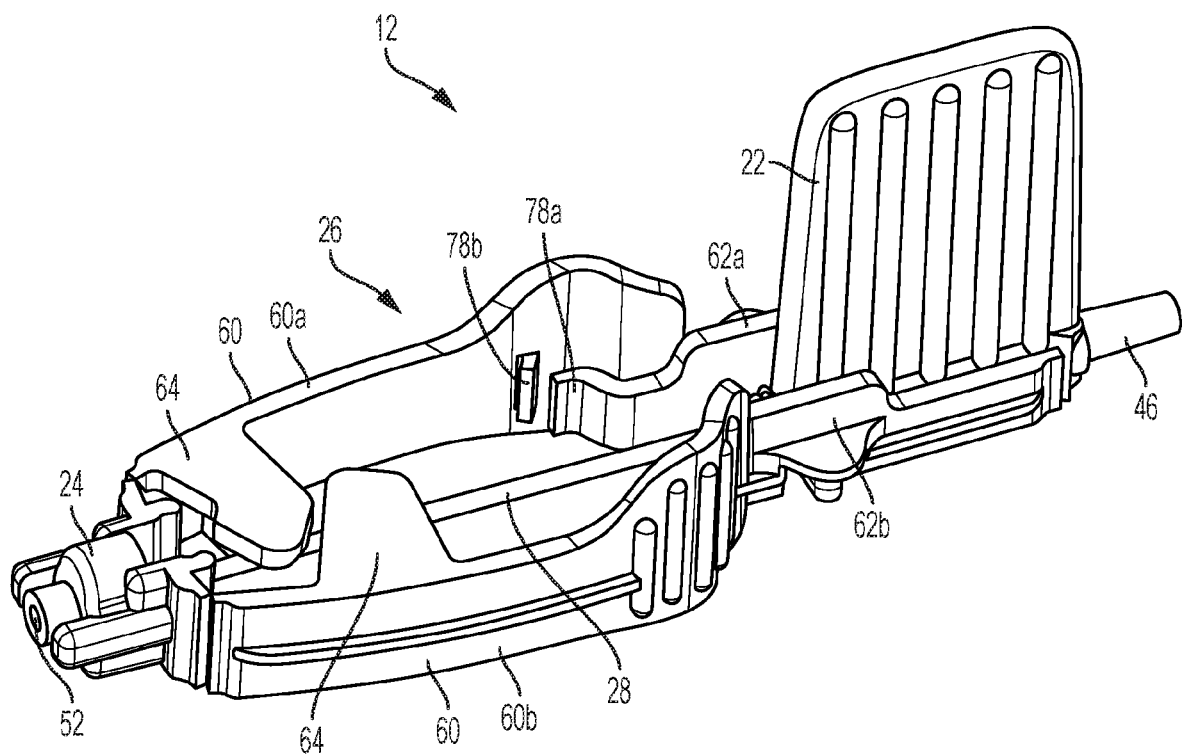
FIG. 6 is a perspective view of the shieldable needle device of FIG. 3, with the tip guard in an extended distal position, in accordance with an embodiment of the present invention.
Figure 7:
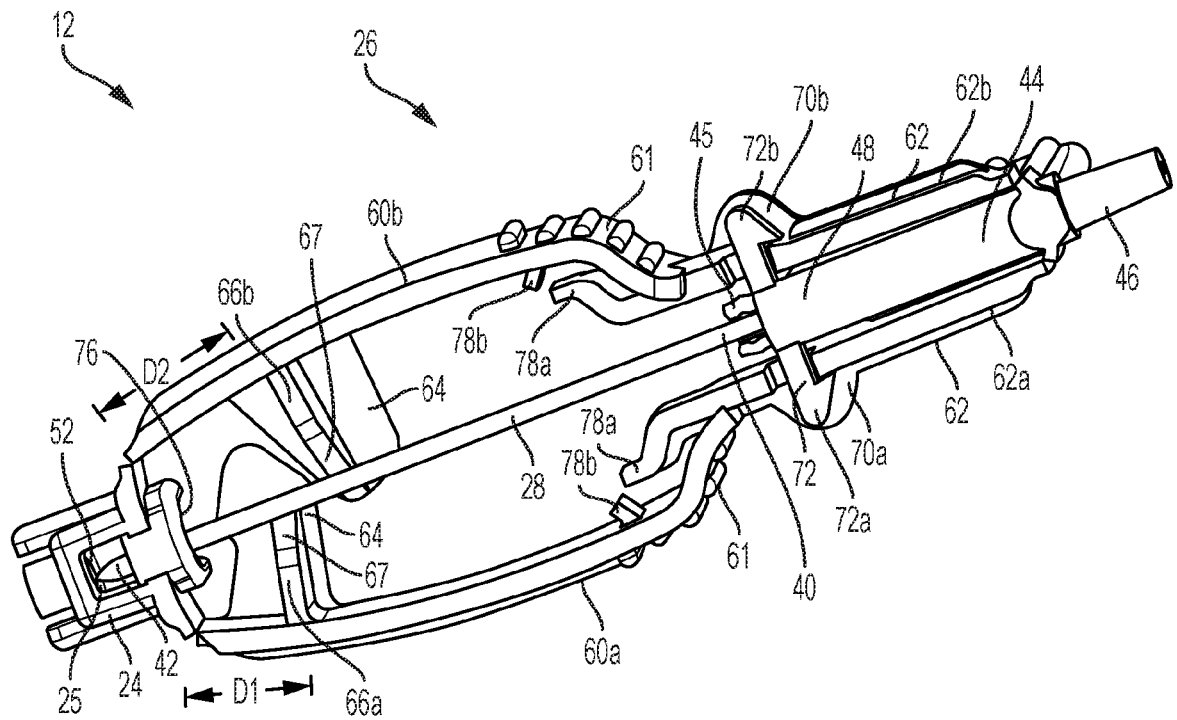
FIG. 7 is a bottom perspective view of the shieldable needle device of FIG. 6, in accordance with an embodiment of the present invention.
Figure 8:
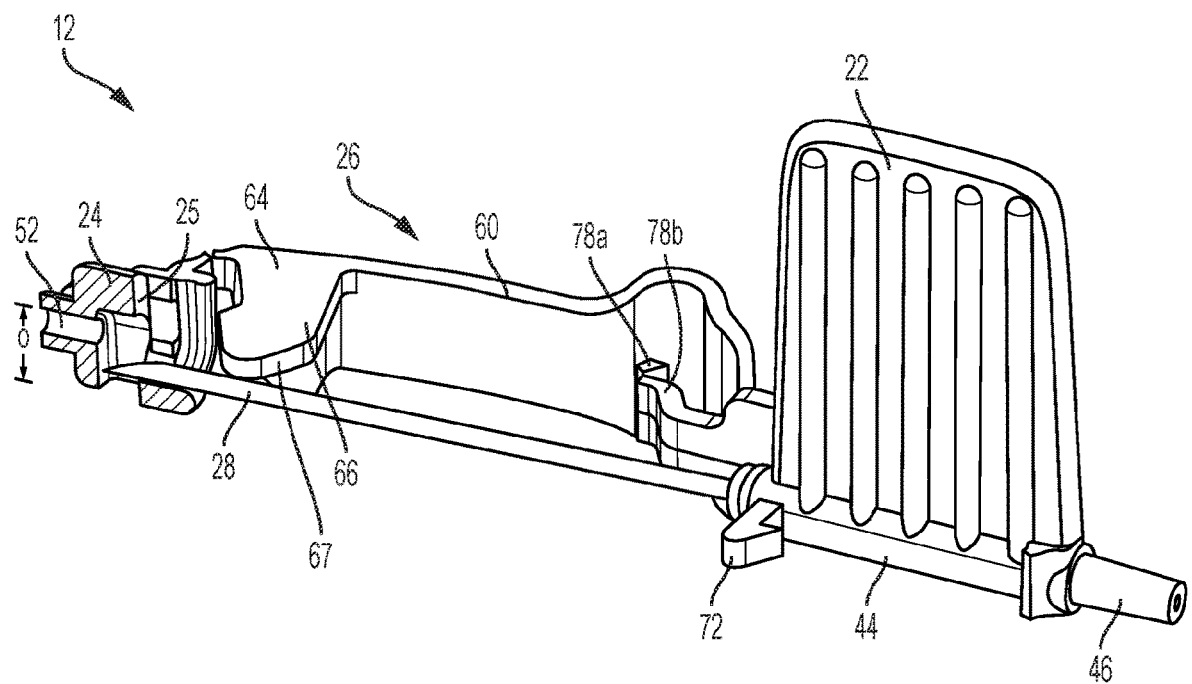
FIG. 8 is a side perspective view of the shieldable needle device of FIG. 6, wherein one of the wings/arms controlling movement of the tip guard has been removed to show the interaction of one of the cannula deflection pads or protrusions to cause deflection of the cannula to the offset position with respect to an opening in the tip guard when the tip guard in in the extended distal position, in accordance with an embodiment of the invention.

With continuing reference to FIGS. 1-4 and with further reference to FIGS. 5, 5A, 5B, and 6-9, upon removal of the cannula guard 30, the tip guard 24 is axially movable along the needle cannula 28 from a proximal position adjacent the hub 44, such that, at least the distal end 42 of the needle cannula 28 extends through an opening 52 defined in the tip guard 24 to a distal position, as shown in FIGS. 6-9, wherein the tip guard 24 protectively surrounds the distal end 42 of the needle cannula 28. A pair of wings 60 extend laterally from opposing sides of the tip guard 24 and are connected to the hub 44 via bendable arms 62. The pair of wings 60 are transitionable between a first position and a second position, wherein transition of the pair of wings 60 from the first position to the second position advances the tip guard 24 from the proximal position, as shown in FIGS. 1-5, to the distal position, as shown in FIGS. 6-8.

Figure 9:
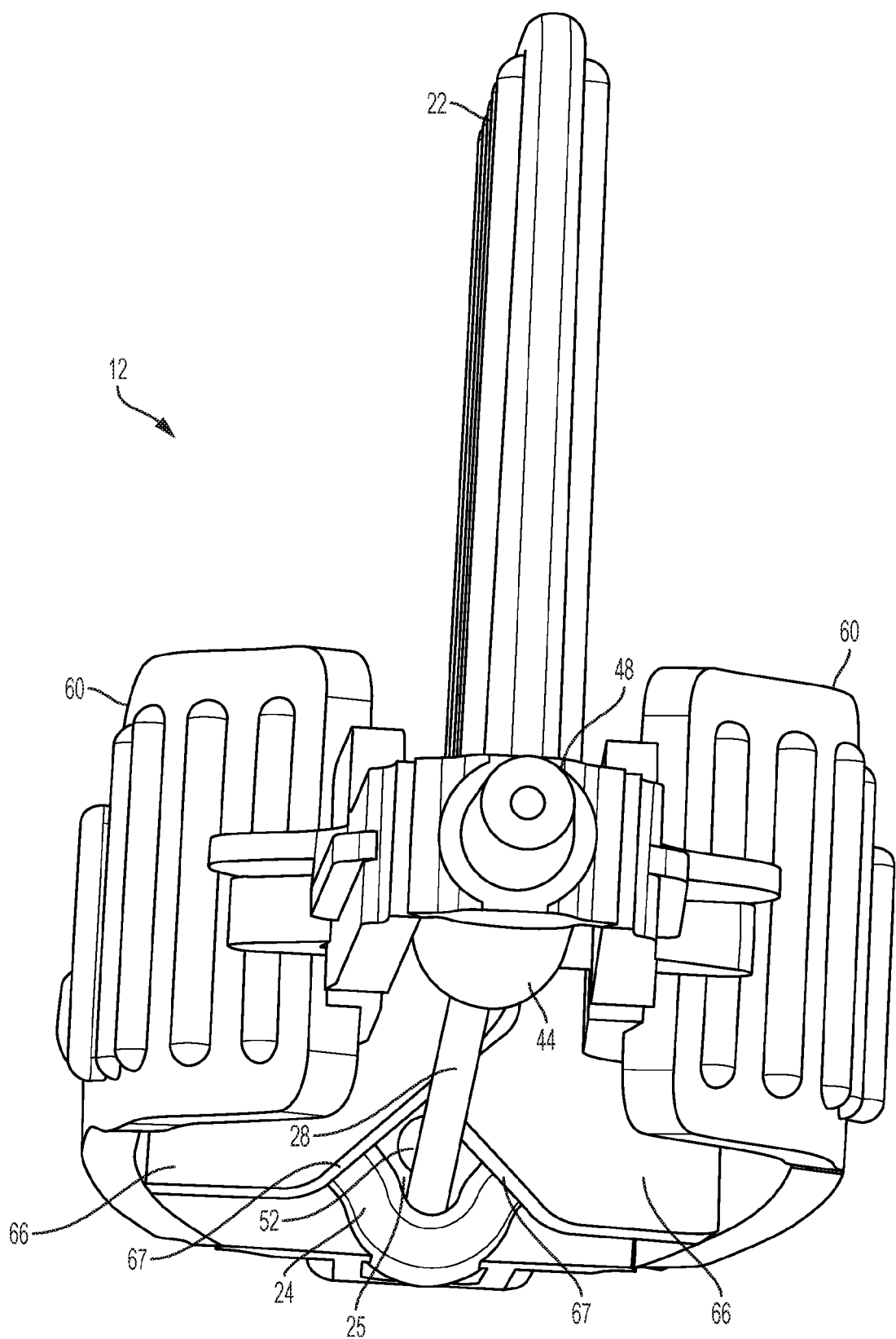
FIG. 9 is a back perspective view of the shieldable needle device of FIG. 6 showing the needle cannula in the offset position with respect to the opening in the tip guard when the tip guard is in the extended distal position, in accordance with an embodiment of the invention.

The wings 60 include tabs 64 that have protrusions 66 extending therefrom, which contact the needle cannula 28. The tabs 64 can be flat members that extend perpendicularly from the wings 60. The protrusions 66 can extend perpendicularly from the tabs and can include a tapered or slanted portion 67, such that, as shown in FIGS. 5A and 5B, as the wings 60 and protrusions 66 move along the length of the needle cannula 28, the protrusions 66 and tapered portion 67 applies a gradual force to the needle cannula 28 during advancement of the tip guard along the needle cannula 28 to cause a longitudinal axis of the needle cannula 28 to become offset, as shown by "O", from the opening 52 of the tip guard 24. As shown in FIGS. 8-9, this offset "O" of the needle cannula 28 to an offset position "OP", as shown in FIG. 5, such that the distal end 42 of the needle cannula is positioned adjacent to an inner surface 25 of the tip guard 24 and prevents the needle cannula 28 from being reinserted through the opening 52 of the tip guard 24, after the tip guard 24 has been transitioned to the distal position.

As shown in FIGS. 1-4, prior to and during use of the collection set 10, the tip guard 24 biases the needle cannula 28, such that, at least the distal end 42 of the needle cannula 28 extends through the tip guard 24 when the tip guard 24 is in the proximal position. Prior to use of the collection set 10, the healthcare worker removes the cannula guard 30 and then uses the blood collection set 10 in a substantially the conventional manner by holding the grip 22, which can be in the form of a dorsal fin, and guiding the needle cannula 28 into a targeted blood vessel. The dorsal fin or grip 22 can include ridges thereon to provide friction and assist in the gripping and maneuvering of the blood collection set 10. Upon completion of the medical procedure, the healthcare worker withdraws needle cannula 28 from the blood vessel and exerts a squeezing force "F" on wings 50. Prior to application of the squeezing force "F", the wings are in a first position, wherein the wings extend in a lateral direction with respect to a longitudinal length "L" of the needle cannula 28. The squeezing force "F" applied to the wings 50 must be sufficient to overcome the holding forces of maintaining the tip guard 24 in the proximal position causing the laterally extending wings 60, in the first position as shown in FIGS. 1-4, to transition, as shown in FIGS. 5A and 5B, to a second position, as shown in FIGS. 6-9, wherein the wings 60 extend in a proximal position, which is substantially parallel to and extends along the longitudinal length "L" of the needle cannula 28 as shown in FIG. 4, and the tip guard 24 shields the distal end 42 or tip of the needle cannula 28. Gripping tips or pads 61 can be provided on the wings 60. Ridges 61a or other tactile enhancements can also be provided on the gripping tips or pads 61 to allow for easier manipulation of the collection set 10.

As discussed above and with continuing reference to FIGS. 5B and 7, at least one of the pair of wings or both of the wings 60 comprises tabs 64 having at least one protrusion 66 extending therefrom including a tapered or slanted portion 67 for contacting the needle cannula 28 when the tip guard 24 is in the distal position to bias the needle cannula to the offset position "OP", as shown in FIG. 5. The offset position places the needle cannula out of alignment with opening 52 and adjacent an inner surface 25 of the tip guard 24, as shown in FIGS. 7-9, to prevent the distal end 42 of the needle cannula 28 from being reinserted through the opening 52 of the tip guard 24 once the tip guard 24 has transitioned from the proximal position to the distal position. According to one embodiment, a first protrusion 66a can be provided on a tab 64 of a first one 60a of the pair of wings 60 at a first distance "D1" from the tip guard 24 and a second protrusion 66b can be provided on a tab 64 of the other one 60b of the pair of wings 60 at a second distance "D2" from the tip guard 24. The first distance "D1" can be different from the second distance "D2". It is further anticipated herein that at least one of the first protrusion 66a and the second protrusion 66b may include a lock feature for locking onto a portion of the needle cannula.

Each of the wings 60 can be connected to the hub by a bendable arm 62. As shown in FIGS. 3 and 4, each bendable arm 62 extends laterally from opposing sides of the hub 44. It can be appreciated that the wings 60, bendable arms 62, tabs 64, and protrusions 66 can be formed by any known material having sufficient strength to deflect the needle and maintain the tip guard 24 in the extended proximal position. A locking edge 70 is provided on at least one of the bendable arms 62. According to one embodiment, a first locking edge 70a can be provided on a first bendable arm 62a, and a second locking edge 70b can be provided on a second bendable arm 62b. According to one embodiment, the bendable arms 62 extend laterally from the hub 44 when the tip guard 24 is in the proximal position and collapse toward and extend along the longitudinal axis "L" of the needle cannula 28 when the tip guard 24 is in the distal position.

The hub 44 can further comprise a locking member 72 adapted to engage with each locking edge 70 to lock the pair of wings 60 in the second position. According to one embodiment, the locking member 72 can comprise a protrusion having a one-way barb for receipt within the locking edge 70. The needle device is designed so that when the locking member 72 engages with the locking edge 70, the locking member 72 is locked to the at least one of the bendable arms 62 at a location proximal to the pair of wings 60. According to one embodiment, the first bendable arm 62a can include a first locking edge 70a configured to engage with a first locking member 72a and the second bendable arm 62b can include a second locking edge 70b configured to engage with a second locking member 72b to lock the first and second wings 60a, 60b in the second position. Because the locking edges 70 of the wings 60 cooperate with locking members 72 located on the hub 44 itself, as opposed to the wings 60, locking onto the needle cannula 28 or to each other, increased stability of the overall blood collection set 10, when the tip guard 24 is extended, is achieved.

Prior to use, the tip guard 24 can be releasably connected to the hub 44 when the tip guard 24 is in the proximal position. According to one embodiment, the hub 44 includes an extension 45 that can be friction fit within a recess 76 defined in the tip guard 24 when the tip guard 24 is in the proximal position. According to one design, the wings 60 and the bendable arms 62 can be connected via a frangible tab 78 when the tip guard 24 is in the proximal position. With reference to FIGS. 5A and 5B, upon application of a sufficient amount of inwardly directed force "F" to the pair of wings 60, this frangible tab 78 is broken, as shown by 78a and 78 b in FIGS. 6-8, allowing the wings 60 and bendable arms 62 to transition from an axially extending position to a proximally extending position, moving the tip guard 24 from the retracted to the extended position such that the tip guard 24 extends about the distal end 42 of the needle cannula 28. As the wings 60 extend or transition, the tapered portion 67 of the protrusions 66 slide along the needle cannula 28 and force the needle cannula 28 to become offset with respect to the initial longitudinal axis "L" to a final biased offset position "OP", as shown in FIG. 5. This final offset position "OP" is out of alignment with the opening 52 of the tip guard 24, and the tapered portion 67 maintains the bias on the needle cannula 28 so that the distal end 42 of the cannula 28 is located adjacent the inner surface 25 of the tip guard 24, as illustrated in FIGS. 7-9, which prevents the distal end 42 of the needle cannula 28 from entering back into the opening 52. This in turn prevents the tip guard 24 from sliding in the proximal direction and inadvertently exposing the distal end 42 of the needle cannula 28, thus reducing the occurrence of needle-stick wounds.

While this disclosure has been described as having exemplary designs, the present disclosure can be further modified within the spirit and scope of this disclosure. This application is, therefore, intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A shieldable needle device comprising:
   a needle cannula having proximal and distal ends;
   a hub secured to the proximal end of the needle cannula;
   a tip guard axially movable along the needle cannula from a proximal position adjacent the hub such that at least the distal end of the needle cannula extends through an opening defined in the tip guard to a distal position where the tip guard protectively surrounds the distal end of the needle cannula; and
   a pair of wings extending laterally from opposing sides of the tip guard and connected to the hub, the pair of wings transitionable between a first position and a second position,
   wherein at least one of the pair of wings comprises a tab extending perpendicularly from the at least one of the pair of wings and a protrusion extending perpendicularly from the tab, wherein transition of the pair of wings from the first position to the second position advances the tip guard from the proximal position to the distal position, wherein the protrusion remains in contact with the needle cannula when the pair of wings are in the second position, and
   the protrusion biases the needle cannula to an offset position (OP) with respect to the opening of the tip guard causing the distal end of the needle cannula to be positioned adjacent to an inner surface of the tip guard preventing the distal end of the needle cannula from being reinserted through the opening in the tip guard after the tip guard has been transitioned to the distal position.

2. The shieldable needle device of claim 1, wherein the tip guard biases the needle cannula such that at least the distal end of the needle cannula extends through the tip guard when the tip guard is in the proximal position.

3. The shieldable needle device of claim 1, wherein each of the wings of the pair of wings comprises the protrusion for contacting the needle cannula during advancement of the tip guard along the needle cannula, and wherein the protrusion on each of the wings remains in contact with the needle cannula when the pair of wings are in the second position.

4. The shieldable needle device of claim 1, wherein a first protrusion is provided on a first one of the pair of wings at a first distance from the tip guard and a second protrusion is provided on the other one of the pair of wings at a second distance from the tip guard, and wherein the first distance is different from the second distance.

5. The shieldable needle device of claim 1, wherein the pair of wings extend laterally in the first position and proximally in the second position.

6. The shieldable needle device of claim 1, wherein each of the wings of the pair of wings are connected to the hub by a bendable arm, each bendable arm extending laterally from opposing sides of the hub, wherein a locking edge is provided on at least one of the bendable arms.

7. The shieldable needle device of claim 6, wherein the bendable arms extend laterally from the hub when the tip guard is in the proximal position and collapse toward a longitudinal axis of the tip guard when the tip guard is in the distal position.

8. The shieldable needle device of claim 1, wherein the tip guard is releasably connected to the hub when the tip guard is in the proximal position.

9. The shieldable needle device of claim 8, wherein the hub is friction fit within a recess defined in the tip guard when the tip guard is in the proximal position.

10. The shieldable needle device of claim 8, wherein the hub and the tip guard are connected via a frangible tab when the tip guard is in the proximal position.

11. The shieldable needle device of claim 10, wherein the frangible tab is broken when an inwardly directed force is applied to the pair of wings.

12. The shieldable needle device of claim 1, further comprising a dorsal fin extending from the hub.

13. The shieldable needle device of claim 1, further comprising a removable guard protectively surrounding the needle cannula when the tip guard is in the proximal position.

14. The shieldable needle device of claim 1, wherein gripping tips are provided on each of the wings of the pair of wings.

15. The shieldable needle device of claim 1, wherein the device further comprises a flexible tube extending from the proximal end of the hub, the flexible tube including structure for mating with a blood collection assembly.

16. A shieldable needle device comprising:
a needle cannula having proximal and distal ends;
a hub supporting at least a portion of the needle cannula;
a tip guard axially movable along the needle cannula from
a proximal position adjacent the hub such that at least the distal end of the needle extends through an opening defined in the tip guard to a distal position where the tip guard protectively surrounds the distal end of the needle cannula; and
a pair of wings extending laterally from opposing sides of the tip guard and connected to the hub, each of the wings connected to the hub by a bendable arm, each bendable arm extending laterally from opposing sides of the hub, wherein a locking edge is provided on at least one of the bendable arms, the pair of wings transitionable between a first position and a second position,
wherein transition of the pair of wings from the first position to the second position advances the tip guard from the proximal position to the distal position,
wherein a longitudinal axis of the needle cannula is offset from the opening of the tip guard preventing the needle cannula from being reinserted through the tip guard after the tip guard has been transitioned to the distal position, and wherein the hub further comprises a locking member adapted to engage with the locking edge to lock the pair of wings in the second position.

17. The shieldable needle device of claim 16, wherein the locking member comprises a one-way barb.

18. The shieldable needle device of claim 16, wherein when the locking member engages with the locking edge, the locking member is locked to the at least one of the bendable arms at a location proximal to the pair of wings.

19. A blood collection set comprising:
a shieldable needle device comprising:
a needle cannula having proximal and distal ends;
a hub permanently secured to the proximal end of the needle cannula;
a tip guard axially movable along the needle cannula from a proximal position adjacent the hub such that at least the distal end of the needle extends through an opening defined in the tip guard to a distal position where the tip guard protectively surrounds the distal end of the needle cannula;
a pair of wings extending laterally from opposing sides of the tip guard and connected to the hub, the pair of wings transitionable between a first position and a second position, wherein the transition of the pair of wings from the first position to the second position advances the tip guard from the proximal position to the distal position; and
a protrusion positioned on at least one of the pair of wings and extending in a perpendicular direction with respect to the at least one of the pair of wings for engaging with and maintaining contact with the needle cannula when the tip guard is in the distal position to bias the needle cannula to an offset position (OP) with respect to the opening of the tip guard causing the distal end of the needle cannula to be positioned adjacent to an inner surface of the tip guard to prevent the distal end of the needle cannula from being reinserted through the opening into the tip guard after the tip guard has been transitioned to the distal position;
a flexible tube having a first end and a second end, the first end of the flexible tube connected to the proximal end of the hub; and
a blood collection assembly secured to the second end of the flexible tube.

20. The blood collection set of claim 19, wherein the blood collection assembly comprises a tube holder and an integrated non-patient cannula.

21. The blood collection set of claim 20, wherein the tube holder is adapted to receive an evacuated specimen collection container therein.

22. The blood collection set of claim 19, further comprising a removable guard protectively surrounding the needle cannula when the tip guard is in the proximal position.

* * * * *